United States Patent [19]

Mazzanobile et al.

[11] Patent Number: 5,094,843
[45] Date of Patent: Mar. 10, 1992

[54] ANTIMICROBIAL TOOTHPASTE

[75] Inventors: Salvatore Mazzanobile; Nader Ibrahim, both of Parsippany, N.J.

[73] Assignee: Beecham Inc., Philadelphia, Pa.

[21] Appl. No.: 579,694

[22] Filed: Sep. 10, 1990

[51] Int. Cl.$^5$ .......................... A61K 7/16; A61K 7/18; A61K 7/26

[52] U.S. Cl. ......................... 424/52; 424/49; 424/58

[58] Field of Search ..................... 424/49-52, 424/58

[56] References Cited

U.S. PATENT DOCUMENTS

| | | | |
|---|---|---|---|
| 1,526,940 | 2/1925 | Staegemann | 424/58 |
| 3,164,524 | 1/1965 | Fand et al. | 167/93 |
| 4,209,505 | 6/1980 | Mikhail | 424/54 |
| 4,272,513 | 6/1981 | Gaffar | 424/52 |
| 4,645,662 | 2/1987 | Nakashima et al. | 424/49 |
| 4,716,036 | 12/1987 | Schelm | 424/57 |
| 4,830,221 | 5/1989 | Mazzanobile | 424/40 |
| 4,945,087 | 7/1990 | Talwar et al. | 424/49 |
| 4,950,479 | 8/1990 | Hill et al. | 424/49 |
| 4,973,472 | 11/1990 | Morisaki | 424/49 |

OTHER PUBLICATIONS

"Euthymol Toothpaste", sold only in the U.K. (unpublished analysis shows: 0.12% Thymol, 1.26% Methyl Salicylate, 0.07% Menthol, and 0.012% Eucalyptol).
Axelson et al, J. Clin. Periodontol, 14(4):205-212 (1987), in B.A., 84: 18507 (1987).
DePaola et al., J. Clin. Periodontol 16(5): 311-315 (1989) in B.A. 88:23479 (1989).
Overholser et al., J. Clin. Periodontol. 17(8):575-579 (1990) in GA. 114:493352 (1991).
"Approval of Listerine, the Background", Biological Therapies in Dentistry, vol. 3, No. 11, Apr. 1988 (approved in 1987) pp. 37-40.
Reg.T.M. 58085 Dec. 4, 1906 (Parke. Davis & Co) "Euthymol Dentifrice Paste", First Used in Commerce Jan. 1896 (in third renewal).

Primary Examiner—Shep K. Rose
Attorney, Agent, or Firm—Rosenamn & Colin

[57] ABSTRACT

A storage stable, anti-plaque and anti-gingivitis toothpaste comprises an amount.

8 Claims, No Drawings

ANTIMICROBIAL TOOTHPASTE

The present invention relates to an antimicrobial toothpaste useful in the treatment of plaque and gingivitis in humans.

Antimicrobial toothpastes have been proposed for the treatment of gum disease using a wide variety of antimicrobial agents, but none has achieved widespread commercial use. The formulation of an antimicrobial toothpaste must satisfy several, often conflicting, requirements. First, of course, the antimicrobial toothpaste must provide a statistically significant therapeutic effect in humans. Those skilled in the art are justifiably skeptical of in vitro tests, even those using art-recognized in vitro models, because often the expected correlation between in vitro activity and activity in humans does not exist in fact.

In addition, the antimicrobial toothpaste must not be irritating to the oral cavity. As is well known, the use of antimicrobial agents in the oral cavity is often accompanied by unacceptable irritation of the oral cavity. While such harsh antimicrobial agents may be safely applied by a dentist on an infrequent basis as part of an annual check-up or the like, they are unsuited for daily use by consumers in the form of an over-the-counter (OTC) toothpaste.

Moreover, to be commercially successful, an antimicrobial toothpaste must have the properties essential to an OTC toothpaste, such as storage stability (i.e. long shelf life), acceptable taste, proper mouthfeel and the like. It is notorious that antimicrobial agents previously proposed for use in toothpastes have had an unacceptable and often extremely unpleasant taste.

In the past, one or more of these requirements has thwarted the widespread acceptance of an OTC antimicrobial toothpaste. The present invention now provides an antimicrobial toothpaste, suitable as an OTC toothpaste, wherein the antimicrobial agent consists essentially of thymol, methyl salicylate, eucalyptol and menthol. Based on clinical data, regular use of the antimicrobial toothpaste of the invention will reduce supragingival plaque and gingivitis and will not be irritating to the oral cavity. In addition, the antimicrobial toothpaste of the invention has the necessary properties for an OTC toothpaste, including acceptable taste.

It is well known that dental plaque is harmful to the gums. Secretions from the bacteria associated with dental plaque include acid, which is involved in the formation of caries, and enzymes and endotoxins, which can irritate the gums and cause gingivitis. Gingivitis, in turn, is usually the precursor of pyorrhea and periodontal disease. By providing an OTC antimicrobial toothpaste that is safe, effective and of acceptable cosmetic properties, particularly taste, the present invention makes available to the consumer the means for conveniently promoting oral hygiene in general and for reducing dental plaque and gingivitis in particular.

According to the present invention, a storage stable, anti-plaque toothpaste having consumer-acceptable taste is provided comprising an orally acceptable dental vehicle, a fluoride ion source effective to provide an anticaries effective amount of fluoride ion, a dental abrasive and an amount effective for reduction of dental plaque and gingivitis in humans of an antimicrobial agent consisting essentially of from about 0.15 to about 0.80% thymol, from about 0.15 to about 1.00% methyl salicylate, from about 0.25 to about 0.80% eucalyptol and from about 0.15 to about 0.60% menthol, preferably from about 0.15 to about 0.45% thymol, from about 0.15 to about 0.45% methyl salicylate, from about 0.25 to about 0.50% eucalyptol and from about 0.15 to about 0.35% menthol, all by weight based on the total weight of the toothpaste.

The present invention is based on the discovery that the antimicrobial agent used in the antimicrobial toothpaste is safe and effective in the treatment of plaque and gingivitis in humans, has an acceptable taste suitable for an OTC toothpaste, and is compatible with conventional ingredients used in an OTC toothpaste, such as fluoride, detergents, coloring agents and the like, so that the resulting toothpaste has acceptable cosmetic properties. Moreover, the acceptable taste of the toothpaste is obtained without the need for special flavor-masking agents often found in the antimicrobial agents of the prior art.

The antimicrobial toothpaste of the invention contains a suitable source of fluoride ion, such as alkali metal fluorides, preferably sodium fluoride, alkali metal monofluorophosphates, stannous fluoride and the like. Preferably, however, the fluoride ion source is an alkali metal fluoride, most preferably sodium fluoride, since this appears to provide enhanced storage stability as compared to other fluoride ion sources. The fluoride ion source is used in an amount to provide an anticaries effective amount of fluoride ion, such as an amount sufficient to provide from about 25 ppm to about 3500 ppm, preferably about 1150 ppm, fluoride.

Any suitable dental abrasive may be used in the toothpaste according to the present invention such as silica dental abrasives, calcium carbonate, dicalcium phosphate dihydrate, $\beta$-calcium pyrophosphate, insoluble alkali metal metaphosphates, plastic dental abrasives, etc. Preferably, however, a silica dental abrasive is used.

Silica dental abrasives are well known, are commercially available and generally have an average particle size ranging between about 0.1 to about 30 microns, such as from about 5 to about 15 microns. Silica dental abrasives useful in the present invention include those marketed by the J. M. Huber Corporation under the trade name "Zeodent" and the silica xerogels marketed by the W. R. Grace and Company, Davison Chemical Division under the trade name "Syloid" U.S Pat. Nos. 3,358,230 and 3,862,307 describe silica dental abrasives that are useful in the toothpastes according to the present invention.

Generally, an amount of the dental abrasive suitable for use in the toothpaste of the present invention will be empirically determined to provide an acceptable level of cleaning and polishing, in accordance with techniques well known in the art. Suitably, the toothpaste of the present invention will contain from about 2 to about 40% by weight of the dental abrasive.

In formulating the toothpaste according to the present invention, the anti-plaque and anti-gingivitis antimicrobial agent, fluoride and dental abrasive are incorporated into an orally acceptable dental vehicle, which may be anhydrous but preferably is an aqueous orally acceptable dental vehicle, to form a storage stable semi-solid extrudable material useful as a toothpaste. As is conventional, the orally acceptable dental vehicle will comprise a binder or thickener, such as natural and synthetic gums, e.g., xanthan gum, carageenates, alginates, cellulose ethers and esters, silica and the like. In formulating the preferred aqueous orally acceptable dental vehicle, a suitable humectant is preferably employed, such as glycerin, sorbitol, propylene glycol or a polyethylene glycol.

In addition, the orally acceptable dental vehicle may include optional ingredients, such as detergents, flavoring agents, sweetening agents, anticaries agents in addition to the fluoride ion source, anti-calculus agents, tooth desensitizing agents, coloring agents, preservatives and pigments. Useful detergents include the water-soluble salts of the alkyl sulfates having from 10 to 18 carbon atoms in the alkyl moiety, such as sodium lauryl sulfate, but other anionic detergents as well as nonionic, zwitterionic, cationic and amphoteric detergents may also be used. A useful anti-calculus agent comprises a water-soluble alkali metal polyphosphate, e.g. sodium tripolyphosphate and the like, a fluoride ion source and, if desired, a synthetic anionic linear polymeric polycarboxylate having a molecular weight of from about 2000 to about one million.

When the preferred aqueous orally acceptable dental vehicle is employed, the toothpaste of the present invention suitably contains from about 10 to about 80% humectant, from about 0.25 to about 5% detergent, from 0 to about 5% sweetener and flavoring agent, together with water and an effective amount of a gelling agent, binder or thickener, such as from about 0.1% to about 15%, to provide the toothpaste of the invention with the desired stability and flow characteristics.

Conventional manufacturing techniques are employed to prepare the toothpaste according to the present invention, which will usually have a pH of from about 4 to about 8. The toothpaste of the present invention may be prepared in the form of a paste of a uniform color or in the form of a striped toothpaste. A suitable apparatus for filling toothpaste tubes with striped toothpaste is described in U.K. Patent Specification No. 962,757. In accordance with this patent, toothpastes of different colors are fed through separate tubes of a bundle of tubes that is inserted into a toothpaste container and gradually moved relative to the container as the container is filled.

The toothpaste of the present invention is used by applying the toothpaste to the teeth. Brushing the teeth with the toothpaste of the present invention reduces the formation of dental plaque and gingivitis.

The present invention is illustrated in terms of its preferred embodiments in the accompanying Examples. All parts and percentages referred to in this specification and the appended claims are by weight based upon the total weight of the toothpaste, unless otherwise specified.

EXAMPLE 1

A toothpaste was prepared from the following ingredients:

| INGREDIENTS | % W/W |
|---|---|
| Polyethylene Glycol 400, NF | 3.0000 |
| Xanthan Gum | 0.9000 |
| D&C Red #30 Lake | 0.0170 |
| Sodium Fluoride, USP | 0.2210 |
| Sodium Saccharin | 0.2140 |
| Sodium Benzoate | 0.2000 |
| Sorbitol 70%, USP | 36.6400 |
| FD&C Blue #1 | 0.0003 |
| D&C Yellow #10 | 0.0001 |
| Hydrated Silica (Dental Abrasive) | 14.0000 |
| Hydrated Silica (Thickener) | 10.0000 |
| Glycerine, 99.0%, USP | 10.0000 |
| Citrus Mint Flavor | 1.0000 |

-continued

| INGREDIENTS | % W/W |
|---|---|
| Sodium Lauryl Sulfate, NF | 1.3000 |
| Titanium Dioxide, Technical Grade | 0.9560 |
| Thymol | 0.2910 |
| Methyl Salicylate | 0.3240 |
| Eucalyptol | 0.3890 |
| Menthol | 0.2260 |
| Deionized Water | Q.S. |
| | 100.0000% |

In these formulas, the humectant was composed of PEG-8 (polyethylene glycol), sorbitol and glycerin, the binder and thickening agents were xanthan gum and hydrated silica. The citrus mint flavor contained 16% of menthol, but no thymol, methyl salicylate or eucalyptol.

The toothpaste had a pH of about 6.3.

Toothpaste prepared in accordance with this Example exhibited excellent cosmetic properties including acceptable taste and storage stability.

EXAMPLE 2

A three-month single blind, randomized, parallel group study was conducted to compare the antimicrobial dentifrice of Example 1 to a control dentifrice containing sodium fluoride but without the anti-plaque and antigingivitis agent of the toothpaste of Example 1.

Adults were examined for the presence of mild supragingival plaque and gingivitis. Subjects were admitted into the study based on a minimum gingivitis index of 0.5 according to the Lobene Noninvasive Modification of the LoeSilness Index. Plaque was measured using the Turesky Modification of Quigley-Hein. A total of 56 subjects were entered into the study.

Qualified subjects were assigned to dentifrice groups by random permutations of two. Thirty subjects were assigned the toothpaste of Example 1 and 26 the control toothpaste. All subjects received a complete oral prophylaxis to remove all supragingival plaque, calculus and extrinsic tooth stain. Subjects were then provided with the assigned toothpaste, a new soft bristle toothbrush and instructions to brush twice daily for one minute. The use of other dentifrices, mouthrinses, oral irrigation equipment and toothpicks was prohibited during the trial. Plaque and gingivitis was scored after 6 weeks dentifrice use and after 12 weeks use.

The results of this trial showed that both plaque and gingivitis were retarded to a greater degree in the subjects using the toothpaste of Example 1, compared to those using the control, conventional fluoride toothpaste. The effect on plaque and gingivitis was visible after only six weeks use and after 12 weeks the difference between the active and control groups was 18% for gingivitis and 20% for plaque. The difference in plaque and gingivitis scores after 12 weeks treatment reached statistical significance ($P\ 0.08$, $P\ 0.03$ respectively) in a one tail T test.

The subjects using the toothpaste of Example 1 found the taste to be acceptable.

It was concluded from this trial that regular use of the antimicrobial toothpaste of the invention reduces dental plaque and gingivitis by 18–20% as compared to a conventional fluoride toothpaste.

I claim:

1. A storage stable, anti-plaque and anti-gingivitis toothpaste having consumer acceptable taste, comprising an orally acceptable dental vehicle, a fluoride ion source effective to provide an anti-caries effective amount of fluoride ion, a dental abrasive and an amount effective for reduction of dental plaque and gingivitis in humans of an antimicrobial agent consisting essentially of from about 0.15 to about 0.80% thymol, from about 0.15 to about 1.00% methyl salicylate, from about 0.25 to about 0.80% eucalyptol and from about 0.15 to about 0.60% menthol, all by weight based on the total weight of the toothpaste.

2. The toothpaste according to claim 1, wherein said anti-microbial agent consists essentially of from about 0.15 to about 0.45% thymol, from about 0.15 to about 0.45% methyl salicylate, from about 0.25 to about 0.50% eucalyptol and from about 0.15 to about 0.35% menthol.

3. The toothpaste according to claim 1, wherein said dental abrasive is a silica dental abrasive, calcium carbonate, dicalcium phosphate dihydrate, β-calcium pyrophosphate, an insoluble alkali metal metaphosphate or a plastic dental abrasive.

4. The toothpaste according to claim 1, wherein said dental abrasive is a silica dental abrasive.

5. The toothpaste according to claim 1, wherein said orally acceptable dental vehicle is aqueous.

6. The toothpaste according to claim 1, including an anti-calculus agent.

7. The toothpaste according to claim 6, wherein said anti-calculus agent comprises sodium tripolyphosphate and said fluoride ion source.

8. A method of treating humans suffering from dental plaque and gingivitis, which comprises applying to the teeth of the sufferer the anti-plaque and anti-gingivitis toothpaste of claim 1.

* * * * *